United States Patent
Barral et al.

(10) Patent No.: US 12,119,110 B2
(45) Date of Patent: Oct. 15, 2024

(54) ROBOTIC SURGERY USING MULTI-USER AUTHENTICATION WITHOUT CREDENTIALS

(71) Applicant: Verily Life Sciences LLC, South San Francisco, CA (US)

(72) Inventors: Joëlle Barral, Mountain View, CA (US); Martin Habbecke, Palo Alto, CA (US); James Shuma, San Jose, CA (US); Robin Thellend, Sunnyvale, CA (US); Brian Carnes, San Jose, CA (US); Neil Inala, San Jose, CA (US); Timothy Chung, Sunnyvale, CA (US); Michael Newton, Palo Alto, CA (US); Michal Levin, Palo Alto, CA (US)

(73) Assignee: VERILY LIFE SCIENCES LLC, Dallas, TX (US)

( * ) Notice: Subject to any disclaimer, the term of this patent is extended or adjusted under 35 U.S.C. 154(b) by 765 days.

(21) Appl. No.: 16/429,346

(22) Filed: Jun. 3, 2019

(65) Prior Publication Data

US 2019/0378610 A1    Dec. 12, 2019

Related U.S. Application Data

(60) Provisional application No. 62/681,434, filed on Jun. 6, 2018.

(51) Int. Cl.
*G16H 40/63* (2018.01)
*A61B 34/30* (2016.01)
(Continued)

(52) U.S. Cl.
CPC ............. *G16H 40/63* (2018.01); *A61B 34/30* (2016.02); *A61B 90/96* (2016.02); *A61B 90/98* (2016.02);
(Continued)

(58) Field of Classification Search
CPC .. G16H 40/10–60; G16H 10/60; A61B 34/40; A61B 90/96; A61B 90/98; G06F 21/31; G06F 21/6245
See application file for complete search history.

(56) References Cited

U.S. PATENT DOCUMENTS

2007/0192137 A1*  8/2007  Ombrellaro ............ G06Q 10/10
                                                    705/2
2011/0207402 A1    8/2011  Perkins et al.
(Continued)

OTHER PUBLICATIONS

Vaucher, Jean, and Hannes Bleuler. "Lifeguard for robotic surgery assistance "LIGRA": An interactive platform centralizing information and control in robotic surgery." 2013 35th Annual International Conference of the IEEE Engineering in Medicine and Biology Society (EMBC). IEEE, 2013. (Year: 2013).*
(Continued)

*Primary Examiner* — Mamon Obeid
(74) *Attorney, Agent, or Firm* — Kilpatrick Townsend & Stockton LLP

(57) ABSTRACT

One example method for robotic surgery using multi-user authentication without credentials includes receiving, by a robotic surgical device, a case code associated with a medical procedure; validating the case code; determining one or more users associated with the case code; and providing access to the one or more users to the robotic surgical device to enable a robotic surgical procedure.

22 Claims, 10 Drawing Sheets

(51) Int. Cl.
  *A61B 90/96* (2016.01)
  *A61B 90/98* (2016.01)
  *G06F 21/31* (2013.01)
  *G06F 21/62* (2013.01)
  *G09B 19/24* (2006.01)
  *G16H 10/60* (2018.01)

(52) U.S. Cl.
  CPC .......... *G06F 21/31* (2013.01); *G06F 21/6245* (2013.01); *G09B 19/24* (2013.01); *G16H 10/60* (2018.01)

(56) References Cited

U.S. PATENT DOCUMENTS

| | | | |
|---|---|---|---|
| 2012/0198531 A1 | 8/2012 | Ort et al. | |
| 2013/0158708 A1* | 6/2013 | Emmertz | G05B 19/0428 700/248 |
| 2013/0191902 A1 | 7/2013 | Friedl et al. | |
| 2014/0180310 A1* | 6/2014 | Blumenkranz | A61B 34/37 901/41 |
| 2017/0049517 A1 | 2/2017 | Felder et al. | |
| 2017/0068785 A1 | 3/2017 | Experton et al. | |
| 2018/0092706 A1* | 4/2018 | Anderson | A61B 34/30 |
| 2019/0206004 A1* | 7/2019 | Shelton, IV | G16H 40/63 |
| 2019/0272917 A1* | 9/2019 | Couture | A61B 34/25 |
| 2019/0282311 A1* | 9/2019 | Nowlin | A61B 34/20 |
| 2019/0287671 A1* | 9/2019 | Mako | G06Q 10/10 |
| 2020/0152311 A1* | 5/2020 | Murphy | A61B 17/60 |
| 2021/0205027 A1* | 7/2021 | Leist | G16H 40/67 |

OTHER PUBLICATIONS

Emerging Technology From the Arx , "Security Experts Hack Teleoperated Surgical Robot", <,https://www.technologyreview.com/s/537001/security-experts-hack-teleoperated-surgical-robot/>, Apr. 24, 2015.

Intuitive Surgical, Inc. , "Onsite for the da Vinci Surgical System Overview", document No. 813331-33 rev C, available at least by Jan. 20, 2018.

King, "Human-Machine Collaborative Telerobotics: Computer Assistance for Manually Controlled Telesurgery and Teleoperation", Dissertation, University of Washington, 2013.

King et al., "Plugfest 2009: Global Interoperability in Telerobotics and Telemedicine", IEEE Int Conf Robot Autom. 2010;2010:1733-1738.

Lum et al., "The RAVEN: Design and validation of a telesurgery system", The International Journal of Robotics Research 28.9 (2009): 1183-1197.

Wozak et al., "End-to-end security in telemedical networks-a practical guideline", International Journal of Medical 8 Informatics 76.5-6 (2007): 484-490,.

Abidin et al., "Crypt-Tag Authentication in NFC Implementation for Medicine Data Management", International Journal of Advanced Computer Science and Applications, vol. 9, No. 9, Jan. 31, 2018, pp. 93-100.

International Application No. PCT/US2019/035448 , "International Search Report and Written Opinion", Sep. 10, 2019, 15 pages.

* cited by examiner

Scheduled Surgeries

Select Date: April 17, 2019

City Central Hospital
- Gall Bladder Removal
  Operating Room: 4C
  09:30
  412
- Gall Bladder Removal
  Operating Room: 4A
  10:00
  414

Metro General Hospital
- Abdominal Tumor Excision
  Operating Room: 2A
  06:00
  414
- Appendectomy
  Operating Room: 1C
  13:00
  412

Johnson Surgical Clinic
- Appendectomy
  Operating Room: 1
  09:00
  414
- Abdominal Tumor Excision
  Operating Room: 2
  15:00
  412

( View or Edit Surgery )
450

User Interface
400

*FIG. 4*

Case Code 600

Case Code 700

Wristband 800
Case Code 600
John Smith
ID: 17423

Surgery File 900
John Smith
ID: 17423
Surgery Materials
CONFIDENTIAL
Case Code 700

ROBOTIC SURGERY USING MULTI-USER AUTHENTICATION WITHOUT CREDENTIALS

CROSS-REFERENCE TO RELATED APPLICATIONS

This application claims priority to U.S. Patent Application No. 62/681,434, titled "Robotic Surgery Using Multi-User Authentication Without Credentials," filed Jun. 6, 2018, the entirety of which is hereby incorporated by reference.

FIELD

The present application generally relates to robotic surgery and user authentication, and more particularly relates to robotic surgery using multi-user authentication without credentials.

BACKGROUND

The use of robotic tools to assist with surgical procedures is becoming increasingly common. The robotic tools may assist with any aspect of surgery, including but not limited to insertion or removal of surgical instruments, resection of tissue, insertion of implanted devices, etc. Such robots may be used for a variety of reasons, including because their movements may be more precise and less prone to transient movements. However, such robots are controlled by one or more persons in an operating room, such as by one or more surgeons. Access to the robot devices is controlled by preventing physical access unless the user is present in the operating room, and by a login name and password to access functions of the robotic device.

SUMMARY

Various examples are described for robotic surgery using multi-user authentication without credentials. One example method for robotic surgery using multi-user authentication without credentials includes receiving, by a robotic surgical device, a case code associated with a medical procedure; validating the case code; determining a one or more users associated with the case code; and providing access to the one or more users to the robotic surgical device to enable a robotic surgical procedure.

Another method includes receiving an identification of a robotic surgical procedure; receiving a selection of a patient for the robotic surgical procedure; receiving a selection of one or more users; associating the patient and the one or more users with the robotic surgical procedure; generating a case code for the robotic surgical procedure; and associating the case code with the robotic surgical procedure.

One example robotic surgical device includes a non-transitory computer-readable medium; a surgical device; a network interface; a case code input interface; and a processor in communication with the non-transitory computer-readable medium, the network interface, and the case code input interface, the processor configured to execute processor-executable instructions stored in the non-transitory computer-readable medium to cause the processor to: receive, from the case code input device, a case code associated with a medical procedure; validate the case code; determine one or more users associated with the case code; and provide access to the one or more users to the robotic surgical device to enable a robotic surgical procedure.

An example non-transitory computer-readable medium comprising processor-executable instructions to cause a processor to receive a case code associated with a medical procedure; validate the case code; determine one or more users associated with the case code; and provide access to the one or more users to the robotic surgical device to enable a robotic surgical procedure.

Another example non-transitory computer-readable medium comprising processor-executable instructions to cause a processor to receive an identification of a robotic surgical procedure; receive a selection of a patient for the robotic surgical procedure; receive a selection of one or more users; associate the patient and the one or more users with the robotic surgical procedure; generate a case code for the robotic surgical procedure; and associate the case code with the robotic surgical procedure.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIGS. 3-5 show example user interfaces for creating or modifying surgery events according to example systems or methods for robotic surgery using multi-user authentication without credentials;

DETAILED DESCRIPTION

Figure 1:
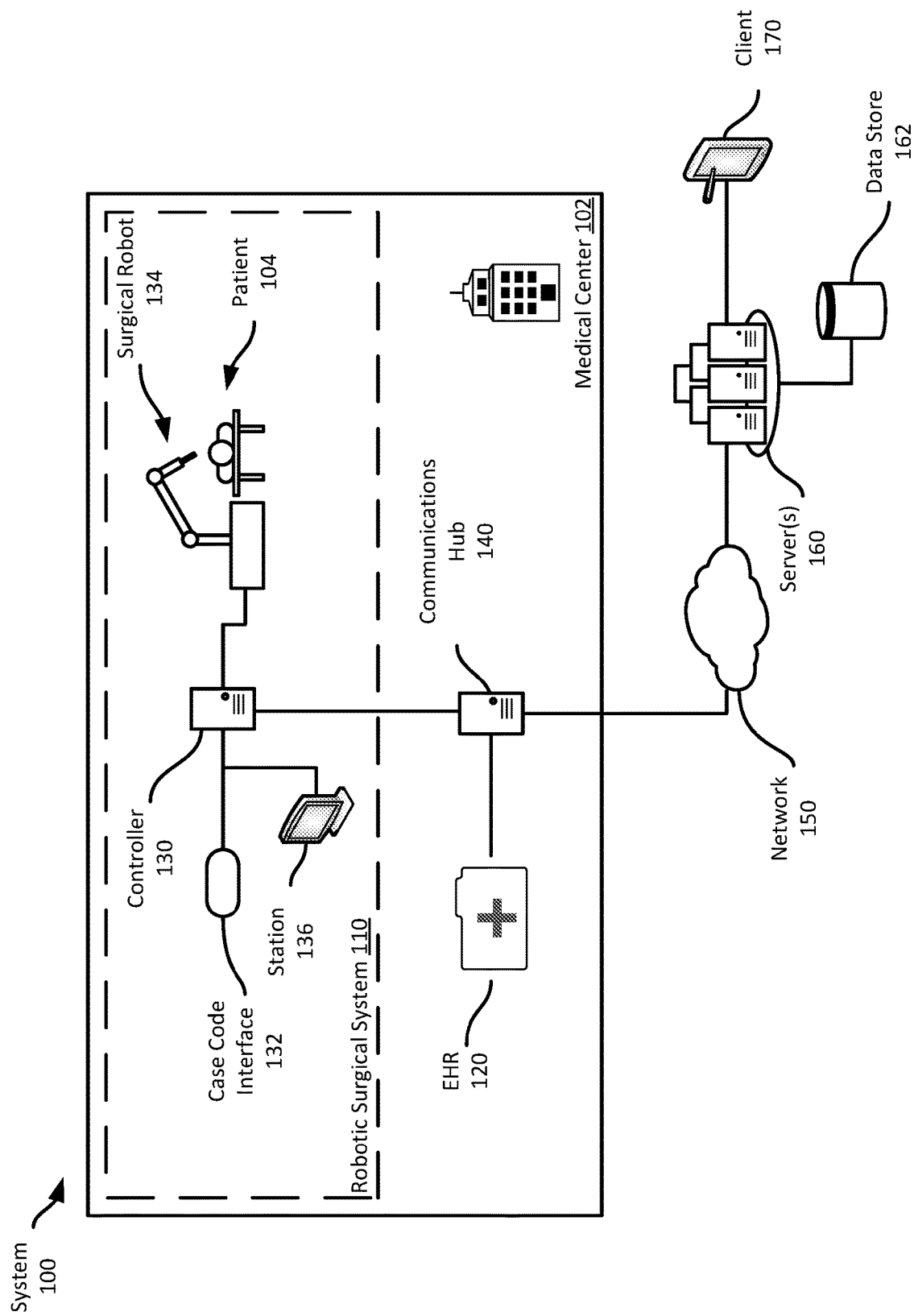
FIGS. 1-2 show example systems for robotic surgery using multi-user authentication without credentials.

Examples are described herein in the context of robotic surgery using multi-user authentication without credentials. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example of a robotic surgery using multi-user authentication without credentials, prior to a surgery, a user, such as the surgeon or an administrator, accesses a web portal or other information service to create a new surgery event. She logs into web portal using a typical authentication method (for example, username and password or multi-factor authentication) and is provided options that may be selected to create the surgery event. In this example, the web portal serves as a central point for multiple medical centers (e.g., hospitals, surgical clinics, etc.), and so the user first selects the medical center where the surgery will take place, City Central Hospital in this case. She then selects an operating room ("OR") and, optionally, the corresponding surgical robot, and a date and time for the surgery. She then accesses patient records, such as copies of patient records received from a surgery scheduling system, to identify the patient to be operated on, the type of surgery to be performed, and the team of doctors, nurses, and other personnel who will participate in the surgery. This may include one or more surgeons, an anesthesiologist, one or more nurses, etc. In addition, one or more patient records or surgery records may be selected as well, including electronic health records ("EHRs").

During the inputting of the information, the web portal confirms whether the requested resources are available, such as the OR and the personnel, and that the requested resources are suitable for the surgery, such as whether the selected surgical robot is capable of or otherwise suitable for the selected surgery and specific patient (e.g., the patient weight is not greater than what the table allows). If any constraints are violated, the user is notified and given an opportunity to make a new selection.

After the surgery has been fully established and all constraints have been satisfied, the user selects an option to save the surgery, at which time, the web portal saves the information and generates a case code for the surgery and associates the case code with the information used to create the surgery as discussed above. The case code in this example is a string of alphanumeric characters generated according to a particular technique so that the case code can be self-authenticated. In this example, the case code is self-authenticating because the case code adheres to a format that can be confirmed using operations performed on the case code itself without comparing the case code to known valid case codes. For example, a case code format may require that the fifth character be an "F," or it may require that a checksum calculated using the case code characters must be stored in the last four digits of the case code, etc. In addition, the case code is uniquely associated with the surgery the user created. Thus, the case code can be used to access the surgery record and obtain the information associated with the surgery records.

After generating the surgery record, the record and corresponding case code are saved to a repository accessible by each of the medical centers. In addition, the case code is printed as a two-dimensional bar code (or QR code) on a surgery ticket, which is provided to one or more members of the surgical team.

When the surgical team arrives for the surgery, one of the team members accesses the surgical robot and presents the surgery ticket to a barcode scanner (e.g., a laser scanner or camera) connected to the surgical robot system. The surgical robot system authenticates the code, and, if the surgery information has already been synced to the robotic surgery device, the surgical team is provided access to it. If it has not already been synced, the system then attempts to obtain the records associated with the surgery, including the identities of the personnel, patient records, surgical setup, and other information about the surgical procedure.

In addition, after authenticating the case code, the surgical robotic system activates the surgical robot itself to allow it to be used in the surgical procedure. If the system has not been able to sync with the repository to obtain the surgery information , it may still allow use of the surgical robot since the case code was authenticated. Ultimately, however, in this example, the authenticated case code provides access to the surgical robot for the surgery team, irrespective of whether the system has synced with the repository.

At the beginning of the surgical procedure, the surgeon, or another member of the team, may identify the surgeon (or multiple surgeons) as operating the surgical robot by selecting her name from the list of surgery personnel obtained from the repository, and the surgical procedure begins.

During the surgical procedure, the system records information generated during the surgery, such as actions taken, information logs, video recording, the user that performed each action, changes in the person operating the robot, etc., and associates the recorded data with the surgery record obtained from the repository. In some examples, the robotic surgical system may provide telestration functionality to enable other surgeons to provide comments or instruction while the robotic surgery is taking place, which may also be recorded. For example, during the procedure, a different surgeon may take control of the surgical robot to perform a portion of the procedure. Upon doing so, a member of the team may record the personnel change by selecting the new operator of the surgical robot. The new surgeon may then perform a portion of the surgery, and other members of the surgical team, or potentially other surgeons observing the surgery may provide comments or instruction, which are then recorded and associated with the new surgeon performing the surgery. At the conclusion of the surgery, the surgical robot system transmits the recorded information to the repository where it is stored with the surgical record. In addition, the case code is invalidated at the repository to prevent its reuse, though in some examples, case codes may be eligible for reuse after a predetermined period of time (e.g., one year).

The example described above provides a convenient way to authenticate use of a surgical robot system without requiring multiple users to each log into the system, which may be difficult with gloves or after scrubbing-in for surgery, or may be skipped entirely. In addition, personnel changes can happen easily with any member able to enter such changes without requiring additional authentication information, or requiring the new user to enter their credentials at the time of the change. In addition, the case code provides a way to uniquely identify the surgery procedure, and a way to provide access to the surgical robot, even if the surgical robot is unable to connect to any other system to validate that the surgery should be occurring and that the personnel is authorized to perform the surgery. Furthermore, because the surgery may involve accessing confidential patient records, e.g., EHRs, subject to federal laws, e.g., HIPAA (the Health Insurance Portability and Accountability Act), the case code can provide a way to authenticate to the medical center or other record keeper that access to the patient records is authorized, log the access by the surgical team, and the relevant records can be retrieved by the robotic surgery system and made available to the surgical team. Thus, examples according to this disclosure may provide a seamless way to create and perform a robotic surgical procedure with reduced security risks, such as shared login and password information, while allowing easy but secure access to confidential patient information, which may include personal health information ("PHI"), by using case codes that are easily presented, but difficult to forge.

This illustrative example is given to introduce the reader to the general subject matter discussed herein and the disclosure is not limited to this example. The following sections describe various additional non-limiting and non-exhaustive examples and examples of robotic surgery using multi-user authentication without credentials.

Referring now to FIG. 1, FIG. 1 shows an example system 100 including a robotic surgical system 110 that employs multi-user authentication without credentials. The example system 100 includes the robotic surgical system 110 located at a medical center 102 that is in communication with one or more remote servers 160 via a communications network 150, such as the Internet. The remote server(s) 160 have an associated data store 162 than may include one or more databases or other servers. A user may use client 170 to access the server(s) 160, such as to create or edit surgeries to be performed.

The robotic surgical system 110 includes a controller 130, a surgical robot 134, and a station 136 usable by personnel in the OR, such as to view surgery information, video, etc., from the surgical robot 134, which may be used to operate on a patient 104 (though the patient is not part of the robotic surgical system 110). In addition, a case code interface 132 is provided and is in communication with the controller 130. The controller 130 is in communication with an optional communications hub 140 that enables, optimizes, or improves communication to the remote server(s) 160 via the network 150. In addition, the communications hub 140 provides access to patient or other medical stored locally at the medical center 102. Further, in some examples the communications hub 140 may operate as a remote server 160, such as in one example in which the communications hub 140 is not local to the medical center 102.

The surgical robot 134 is any suitable robotic system that can be used to perform surgical procedures on a patient, to provide simulations of surgical procedures, or to provide training functionality to allow a surgeon to learn how to control a surgical robot 134, e.g., using exercises to train particular movements or general dexterity, precision, etc. It should be appreciated that discussions throughout this detailed description related to surgical procedures are equally applicable to simulated procedures or training exercises using a surgical robot 134. A surgical robot 134 may have one or more articulating arms connected to a base. The arms may be manipulated by a controller 130, which may include one or more user interface devices, such as joysticks, knobs, handles, or other rotatable or translatable devices to effect movement of one or more of the articulating arms. The articulating arms may be equipped with one or more surgical instruments to perform aspects of a surgical procedure. Different surgical robots 134 may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without articulating arms, such as for endoscopy procedures, may be employed according to different examples.

In some examples, surgical robots (or a respective controller, e.g., controller 130) may be configured to record data during a surgical procedure. For example, the surgical robot 134 may record inputs made by the user, actions taken by the surgical robot 134, times (e.g., timestamps) associated with each input or action, video from one or more cameras of the surgical robot, etc. . In some examples, surgical robot may include one or more sensors that can provide sensor signals, such as thermocouples, pulse sensors, SvO2 or SpO2 sensors, one or more cameras, etc., or other information to be recorded, such as temperatures, pulse information, images, video, etc. Such information may be obtained by the sensor and transmitted to a computing device within the surgical robot 134 itself or to the controller 130 for storage. Furthermore, while only one surgical robot 134 is depicted, any suitable number of surgical robots may be employed within a surgical robotic system 100.

The controller 130 in this example includes a computing device in communication with the surgical robot 134 and is able to control access and use of the robot. For example, the controller 130 may require that a user authenticate herself before allowing access to or control of the surgical robot 134. As mentioned above, the controller 130 may include, or have connected to it, one or more user input devices capable of providing input to the controller, such as a keyboard, mouse, or touchscreen, capable of controlling the surgical robot 134, such as one or more joysticks, knobs, handles, dials, pedals, etc.

In this example, the controller 130 has a case code interface 132 attached to it. The case code interface 132 includes electronics and/or software to obtain a case code to authenticate a surgical team, provide access to the surgical robot 134, and obtain electronic information about the surgery, including patient records. A case code may be provided in many different forms, thus, the case code interface 132 may be any suitable device to accept or obtain a case code. For example, a case code interface 132 may include a keyboard or keypad to manually enter a case code. In some examples, the case code interface may include a barcode reader, a camera, an NFC ("near-field communications") reader, a Bluetooth ("BT") or BT low-energy ("BLE") reader, a magnetic stripe reader, a chip reader, or any other suitable device to obtain a case code. In some examples, the case code interface 132 may be provided on the surgical robot, such as within a camera. At the outset of the surgery, the surgical robot may be manipulated to focus its camera on a case code to receive an image of the case code and provide it to the controller 130. Example case codes will be discussed in more detail below with respect to FIG. 6-15.

In this example, the case code interface 132 can read or otherwise accept a case code and provide it to the controller 130. The controller 130 can then authenticate the case code, and then transmit the case code to a remote server 160 to obtain electronic information about the surgery associated with the case code. For example, the remote server(s) 160 may receive the case code, obtain a surgery record using the case code and obtain information associated with the surgery and transmit it to the controller 130. Such information may include identity information about the personnel assigned to the surgery, the surgery to be performed, information about the patient, which may include one or more patient records, etc. In some examples, the information may include information to enable the controller 130 to request patient records from another computer system. For example, the remote server(s) 160 may provide patient information, such as a patient name or patient identification ("ID") number. The controller 130, after receiving the patient information, may issue a request to another computer system, such as a system local to the medical center, to obtain one or more EHRs 120 associated with the patient. Because such information may include confidential patient information protected by various privacy laws, e.g., HIPAA, the controller 130 may only request such information after authenticating the case code and obtaining the surgery records. The authentication process may provide the necessary authorization to enable access to those records. If the authentication fails, or if the case code is not recognized despite authenticating correctly, the controller 130 may still activate and provide access to the surgical robot, but it may not obtain any patient information unless another case code is provided or until another authentication procedure is performed.

In some examples, a surgery team may employ a default or generic case code to obtain access to and use of a surgical robot. For example, a provided case code may have been damaged or lost; however, the surgery must go forward. Thus, the surgery team may instead enter a default code that is authenticated as a default code and which provides sufficient access to the surgical robot 134 to perform a surgery, but does not enable access to any other information, including patient records.

After obtaining the information, the controller 130 may activate the surgical robot 134, provide access to the surgical robot 134 to the surgery team, and provide access to patient information, including copies of one or more EHR records.

As discussed above, the robotic surgical system 110 includes a communications hub 140 that includes a computer or server that manages communications with the controller 130 and surgical robot 134 within the medical center 102 and provides communications out of the medical center 102 and to the network 150. For example, the communications hub 140 may include a networking device, such as a router or a switch. However, the communications hub 140 may include one or more server devices that provide additional features, such as user access to patient or other medical records received from the server(s) 160, etc., while also providing secure access to locally stored medical records to the controller 130 or surgical robot 134. In some examples, the communications hub 140 is an optional component that may be omitted, or may be a virtual machine running on an underlying computing system.

It should be appreciated that while this example shows only one surgical robot 134 and controller 130 in communication with the communications hub 140, in some examples, the communications hub 140 may be in communication with multiple controllers 130 and surgical robots 134. For example, the medical center 102 may have one communications hub 140 per floor, or one for every four surgical robot 134/controller 130 combination, etc. In some examples, the medical center 102 may only have a single communications hub 140 that is in communication with all controllers 130 and surgical robots 134 at the medical center 102.

The robotic surgical system 110 may also have access to one or more EHRs 120 or other medical records via the communications hub 140. While the EHRs themselves are not a component of the robotic surgical system 110 itself in this example, they may be accessed by a controller 130 or surgical robot 134 and may be stored locally at the medical center 102.

As discussed above, the robotic surgical system 110 is in communication with one or more remote servers 160 via network 150. The network 150 may be any combination of local area networks ("LAN"), wide area networks ("WAN"), e.g., the internet, etc. that enable electronic communications between the communications hub 140 and the remote servers 160.

The remote server(s) 160, in conjunction with the data store 162, store records about one or more surgeries to be performed, previously performed surgeries, medical personnel, medical centers, operating rooms, patients, etc., to enable a user to create new surgeries, schedule them, assign medical personnel, assign a patient, allocate an OR and a robotic surgical system for the surgery, etc. Thus, the server(s) 160 provides management and administrative control over the creation of new surgeries and the access to the data underlying those surgeries, including patient EHRs. It also provides a web portal that a user may access via a client 170 to create new surgeries and manage previously created surgeries.

Thus, the system 100 may enable a user to create a new surgery to be performed, such as by selecting a location for the surgery, assigning a robotic surgical system 110, assigning one or more medical personnel to perform the surgery, schedule the surgery at a particular date and time, assign a patient to be operated on, and select one or more patient records (e.g., EHRs) to be provided for the surgery, and then store the new surgery at the device and create a case code for the surgery. The case code can then be provided to the surgical team (as will be described in more details below) and, at the scheduled time, the surgical team can provide the case code to the robotic surgical system 110 via the case code interface 132 to activate and access the surgical robot 134 and any patient records associated with the surgery. The surgical team can then perform the surgery, record data during the surgery, and upload the data to the remote server(s) 160 during the surgery or after it is completed.

Figure 2:
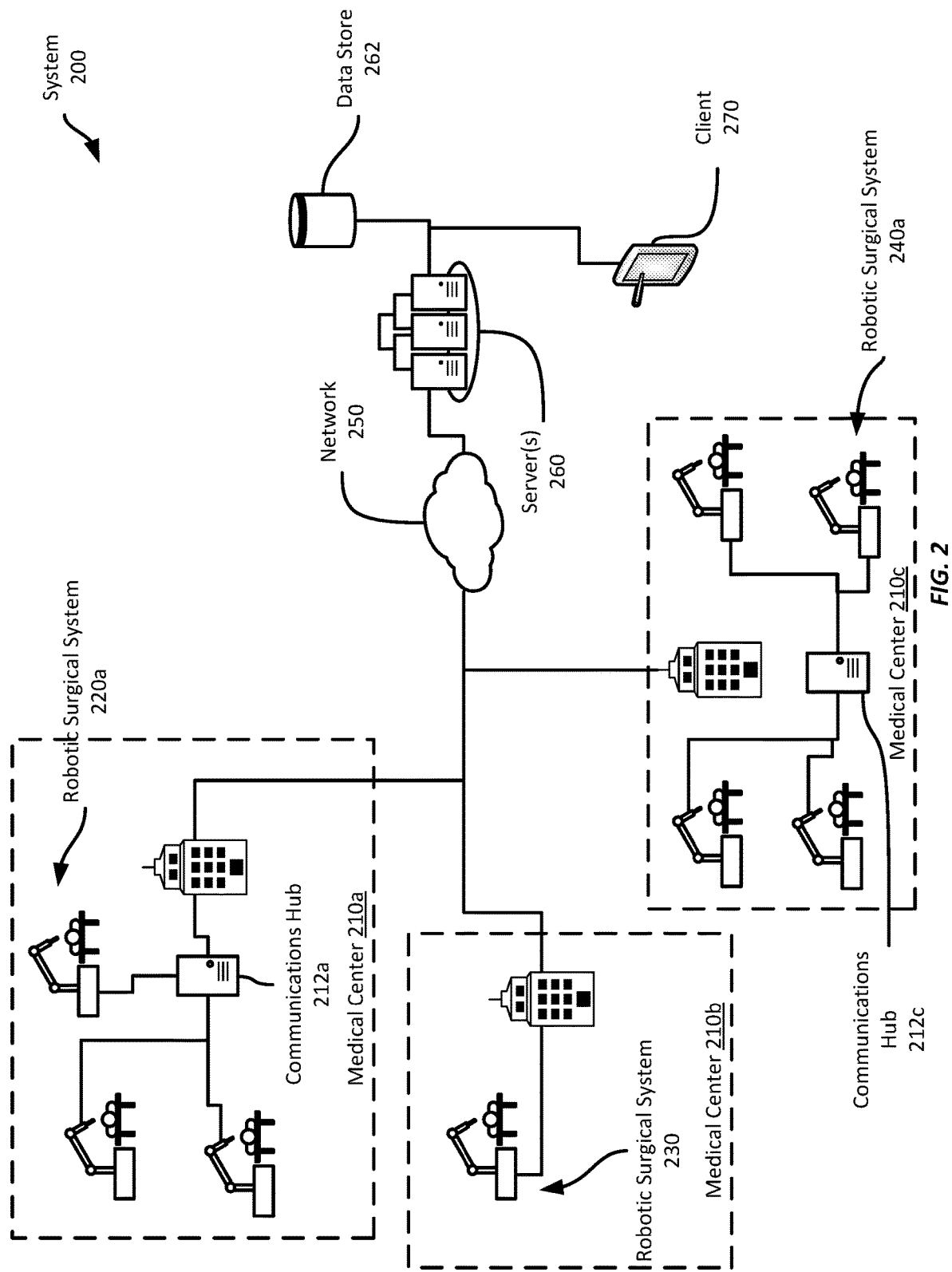

Referring now to FIG. 2, FIG. 2 shows another example system 200 for robotic surgery using multi-user authentication without credentials. In this example, multiple medical centers 210a-c within a medical center network (referring to a group of associated medical centers rather than a type of communications network) are all in communication with a common remote server or group of servers 260. Each medical center 210a-c has one or more robotic surgical systems 220a-c, 230, 240a-d (note that, for space reasons, 220b-c and 240b-d are shown but not labelled). Each robotic surgical system 220a-c, 230, 240a-d is in communication with the remote server(s) 260 via a communications network internal to the respective medical center 210a-c and then via network 250.

In this example, the robotic surgical systems 220a-c, 230, 240a-d comprise an example robotic surgical system according to this disclosure, such as the example robotic surgical system 110 shown in FIG. 1. Thus, each includes a surgical robot, a controller, a station 136, and one or more case code interfaces, such as in the examples discussed above with respect to FIG. 1. One or more may also include a communications hub, or a communications hub may be provided by the medical center 210a-c and may service one or more robotic surgical systems or other equipment at the respective medical center 210a-c.

Similar to the example shown in FIG. 1, the server(s) 260 have an associated data store 262 than may include one or more databases or other servers, and a user may use client 270 to access the server(s) 260, such as to create or edit new surgeries to be performed substantially as described above with respect to FIG. 1.

In this example, the server(s) 260 are shared by multiple medical centers 210a-c. Such an architecture may facilitate the creation of surgeries by a single person or group of people for the group of medical centers 210a-c. Such an arrangement may be of value when medical personnel perform work at multiple different medical centers or if a patient receives treatment at multiple different medical centers. For example, if a particular surgeon is employed to work at two medical centers, such as medical centers 210a-b, a surgery administration team using this example system 200 may be able to effectively schedule the surgeon at both medical centers 210a-b without inadvertently double-booking the surgeon or needing to check schedules at multiple locations to ensure a surgery may be scheduled at a particular time. Rather, the client 270 may be provided access with scheduling information for both medical centers 210a-b and enable more efficient surgery planning as well as more efficient use of the surgeon's time. For example, rather than scheduling the surgeon to move between medical centers multiple times over the course of a day or multiple days, surgeries may be scheduled to reduce or eliminate trips between medical centers 210a-b, or even different ORs, on a single day.

Similarly, if a patient receives treatment at multiple medical centers, the use of a single server (or set of servers) to manage all three medical centers may enable more efficient aggregation of the patient's data, enabling it to be more easily and completely provided to the surgery team prior to the surgery. For example, after scheduling a surgery, the server(s) 260 may obtain patient records from each of the medical centers 210a-c and associate them all with the surgery, thereby enabling the entire set of patient records (or a relevant subset of them) to be provided along with the surgery record to the robotic surgical system when the case code is provided.

Thus, in some examples, multiple robotic surgical systems may be managed by a single client or server (or set of servers), or even multiple medical centers (or groups of medical centers) may be managed by a single set of administrators using a single set of servers. Still more complex arrangements may be employed according to various embodiments.

Figure 3:
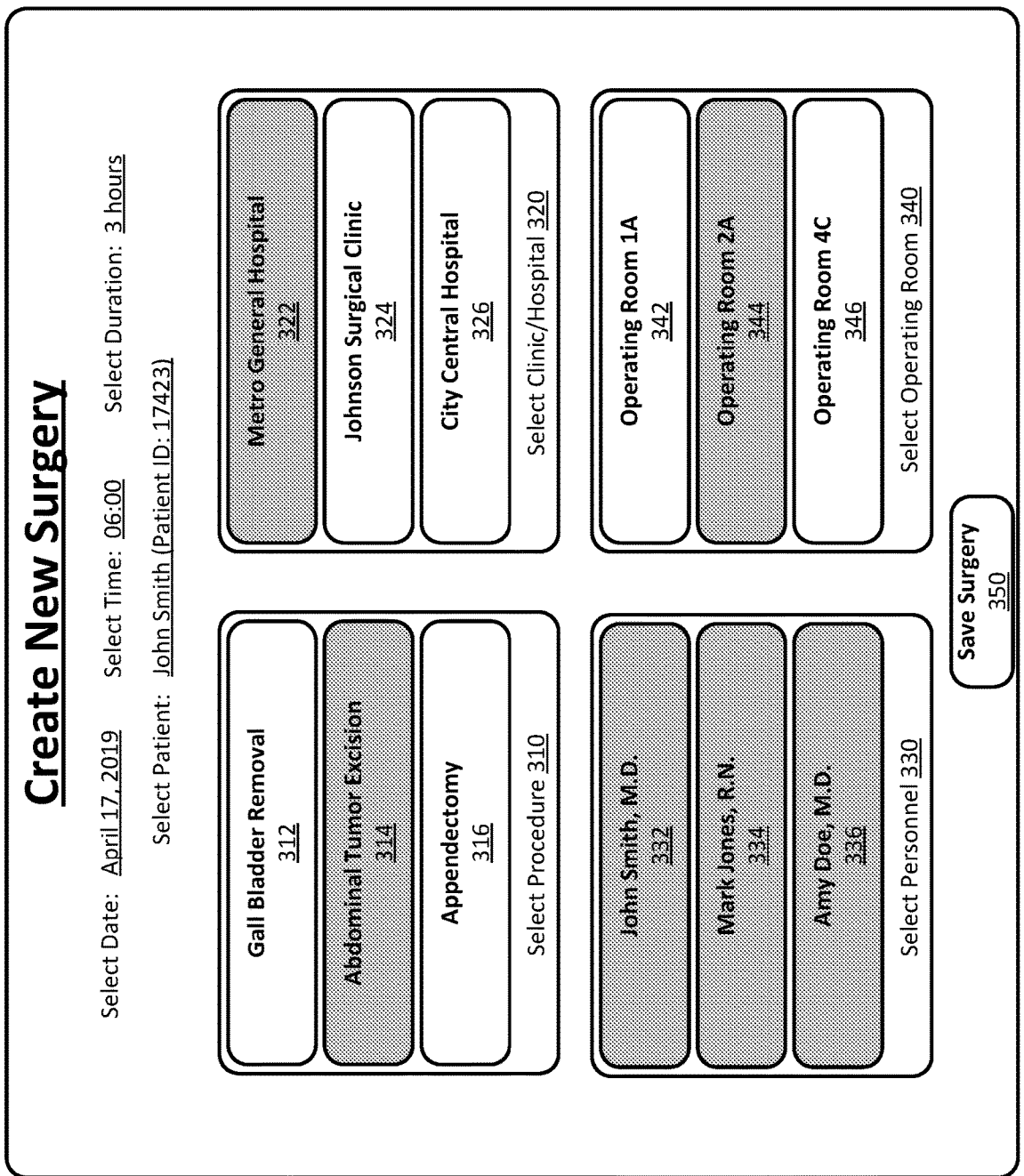

Referring now to FIG. 3, FIG. 3 shows an example user interface 300 for a web portal to create or modify robotic surgeries to be performed at a medical center within a particular network of medical centers. As discussed above with respect to FIGS. 1 and 2, a user may access a web portal using a client device. The web portal may be hosted by one or more remote servers with access to a data store with information about various medical centers, medical personnel, robotic surgery devices, patients, etc. In addition, the remote servers may also have access to scheduling information for robotic surgeries. Thus, access to the web portal may provide the user with access to such information, enabling the user to create or modify surgeries.

In this example, the user accesses the web portal by entering a username and password, or a two-factor authentication scheme involving a username and password as well as a one-time code. After selecting an option to create a new surgery and the patient to be operated on, she is presented with the user interface 300 shown in FIG. 3. The user interface 300 includes categories of options to select a procedure 310, select a medical center 320, select personnel 330 to participate in the surgery, and select an operating room 340. In this example, as the user selects the options for the surgery, the selected options are highlighted to enable the user to quickly review the selected information. In this example, the user has created a new surgery that will be an abdominal tumor excision 314 scheduled on Apr. 17, 2019 at 06:00 at Metro General Hospital 322 in operating room 2A 344. In addition, two doctors and a nurse have been selected to participate in the surgery and the surgery has been scheduled to last three hours. It should be appreciated that while only three options are shown for each category of options 310-340, any number of options may be presented, such as by using scroll buttons, search bars, etc.

After the user has created the surgery, she may select the "Save Surgery" 350 option to save the surgery and store it with the remote server(s) 260, such as in the data store 262. After saving the surgery, it will be registered with the remote server(s) 260 and will provide constraint or conflict information to prevent other surgeries from using the same resources, such as the same OR, robotic surgery system, personnel, patient, etc. during the scheduled surgery.

In addition, after selecting "Save Surgery" 350, the web portal will provide a case code for the surgery. In this example, the case code is generated by a remote server 260 and is associated with the newly created surgery. Example case codes will be discussed in more detail with respect to FIG. 6 below. However, the generated case code uniquely identifies the scheduled surgery and enables access to the scheduled surgery information at the remote server(s) 260, including the type of procedure; the date, time, and location of the surgery; the personnel assigned to the surgery; and the operating room. Still other information may be associated with the surgery, including one or more patient records, including EHRs associated with the patient. In some examples, individual EHRs may be selected to be associated with the surgery; however, all available patient records or information may be associated with the surgery in some examples. Such information can be manually entered, obtained from one or more EHRs, obtained from one or more remote systems, or uploaded, such as in the case of newly-obtained information, e.g., pre-operation images. In some examples patient records may be obtained from the medical center's case management system.

Referring now to FIG. 4, FIG. 4 shows an example user interface 400 of the web portal that enables the user to see the various scheduled surgeries on a particular date. In this example, the user interface 400 shows surgeries scheduled on Apr. 17, 2019 at the three medical centers shown in FIG. 2. In addition, the user interface 400 allows the user to select a scheduled surgery to modify it, or simply view it. In this example, the user has selected an abdominal tumor excision surgery 414 to view, and selects the "View or Edit Surgery" button 450.

Figure 5:
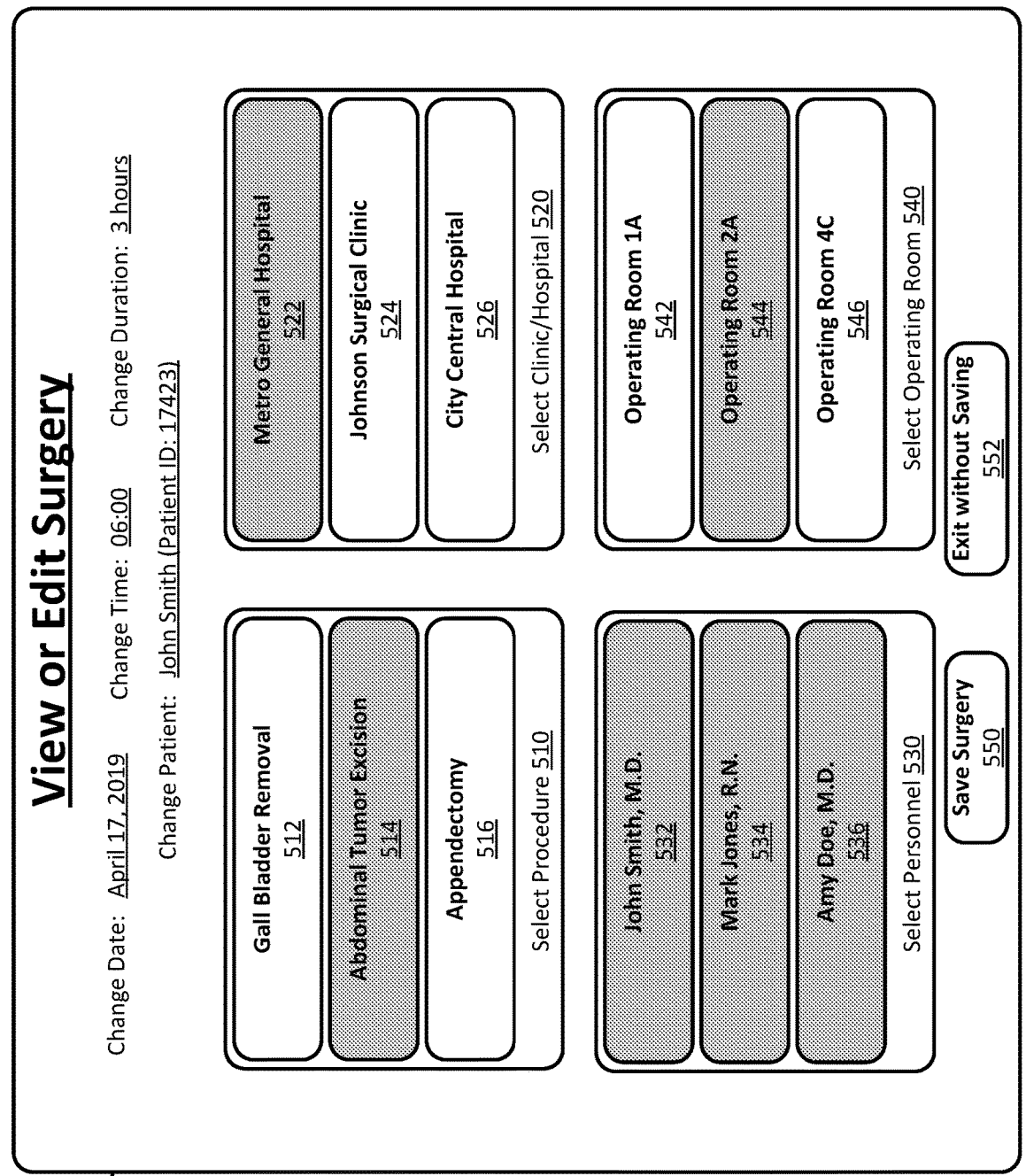

Referring now to FIG. 5, FIG. 5 shows an example user interface 500 of the web portal that enables the user to view or edit a previously created surgery. In this example, the user is shown the options selected for the surgery and also provides other options the user may select to change the scheduled surgery. After making any changes, the user can elect to save the changes 550 or to exit without saving 552. In some examples, the data may be auto-saved as the user works to prevent inadvertent loss of information. If the user saves the changes 550, the remote server(s) 260 update(s) the surgery information and presents it to the user when the user returns to the user interface 400 shown in FIG. 4.

Thus, FIGS. 3-5 illustrate a system for robotic surgery using multi-user authentication without credentials that includes multiple different medical centers, each having robotic surgeries created and scheduled via a common web portal. And while the description of FIGS. 3-5 was in the context of a web portal, other implementations may be employed instead. For example, a user may interact with a mobile app installed on a mobile device, such as a smartphone or table. The mobile app may accept the user input as discussed above and then connect with a remote server(s) 160 to upload the new or modified surgery to the remote server(s) 160.

Figure 6:
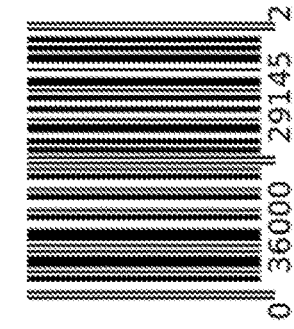
FIGS. 6-7 show example case codes for robotic surgery using multi-user authentication without credentials.
Figure 7:

Referring now to FIGS. 6-7, FIGS. 6-7 illustrate different examples of case codes and different ways a case code can be manifested or otherwise provided to a surgical team to enable use of a surgical robot and access to the surgery information associated with the case code, including patient records (e.g., EHRs). A case code, as discussed above, may be a string of alphanumeric characters that has been generated according to a technique that creates codes that may be self-authenticated to ensure that the case code was validly generated. It should be appreciated that "self-authenticated" does not require that the case code's validity may be entirely determined from the case code itself, e.g., self-authentication does not require that the case code contain the information required to assess its correct formatting, that the case code references a validly scheduled surgery, etc. Rather, in this example, the case code can be self-authenticated to ensure that it was generated according to the correct technique. For example, the format of a case code may require that the last two digits of the case code represent the checksum of the other characters of the case code. Or the format of the case code may require that the first and third characters have a particular format, such as an identifier for a particular medical center and operating room. Still other example case code formats may be employed.

After a case code has been generated, it may be encoded according to any of the examples shown in FIG. 6 or 7, or any other convenient encoding technique. For example, FIGS. 6-7 show examples of case codes that have been manifested as machine-readable codes that may be printed on a label or displayed by a handheld device. In particular, FIG. 6 shows a two-dimensional ("2D") bar code (also referred to as a "QR" code). The 2D bar code encodes the case code generated by, for example, a web portal or a remote server 260. FIG. 7 shows a one-dimensional ("1D") bar code, which may be used instead.

Figure 8:
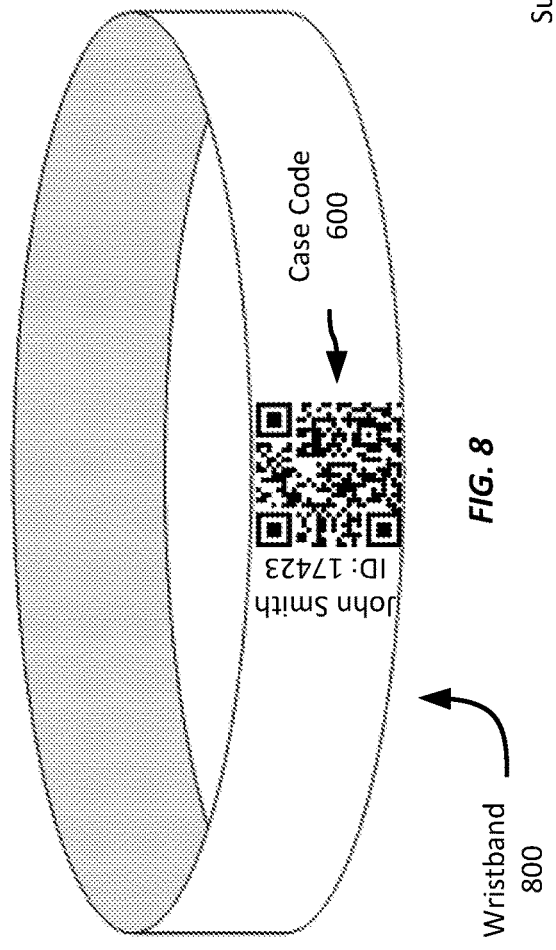
FIGS. 8-9 show example embodiments of case codes for robotic surgery using multi-user authentication without credentials.
Figure 9:
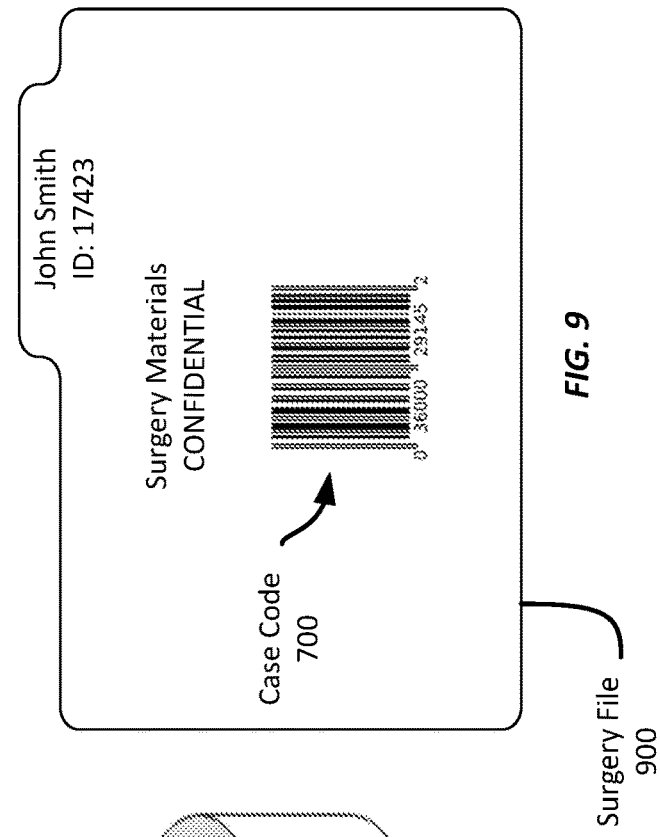

Case codes generated in a bar code format, such as 1D or 2D bar codes, may be printed on a ticket, may be printed on a wristband and provided to the patient to wear, may be printed and affixed to a packet of materials (e.g., a folder) for the surgeon(s). For example, FIG. 8 shows a patient wristband 800 having a 2D bar code 600 printed on it, along with the patient's name and ID number. In FIG. 9, a case code 700 has been affixed to the outside of a folder 900 having surgery materials within it, include patient EHR information. It should be appreciated that any suitable visual representation of a case code may be employed, including techniques such as printing a string of characters, manually writing out the case code, e.g., on a whiteboard, or it may be provided audibly, such as by speaking it aloud or playing an audio clip containing the case code, e.g., by a mobile device or other computing device located within the OR.

In some examples rather than physically printing a copy of the case code, one or more of the assigned medical personnel may be provided an electronic copy of the case code. For example, medical personnel at each of the medical centers associated with the remote server(s) 260 and web portal may be provided with an application (or "app") to install on a mobile device (e.g., a smartphone, tablet, phablet, laptop, etc.) or other computing device. Case codes may then be automatically pushed by the remote server(s) 260 (or other remote computing device) to one or more members of a surgical team when a new surgery is created. Upon arriving at the operating room, a member of the surgical team may launch their copy of the app to obtain the case code. The app may then display the case code on the mobile device's screen, which may be presented to a camera or other case code interface. Alternatively, and as will be discussed in more detail with respect to FIGS. 10-12, the case code may be transmitted by the mobile device to a robotic surgical system using NFC, BT, BLE, or any other suitable wireless communication technique.

Figure 10:
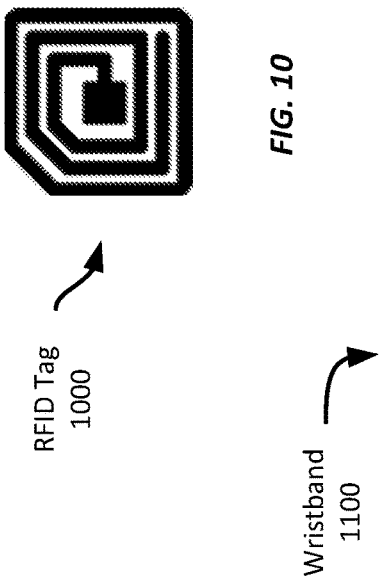
FIG. 10 shows an example RFID tag to store and provide a case code for robotic surgery using multi-user authentication without credentials.
Figure 11:
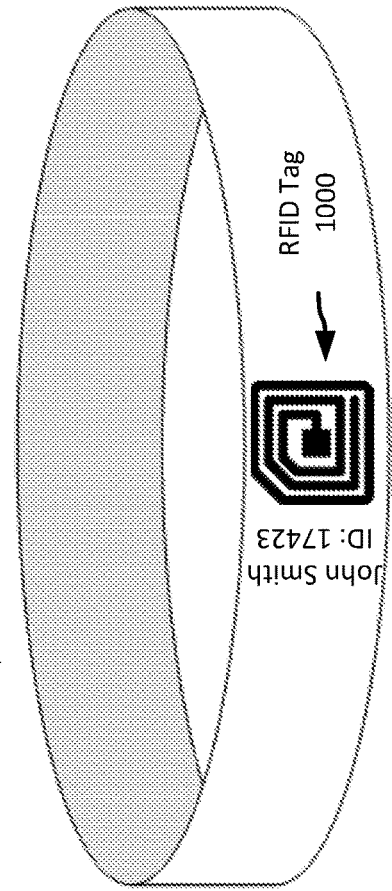
FIG. 11 shows an example wearable device having an RFID tag to store and provide a case code for robotic surgery using multi-user authentication without credentials.

Referring now to FIG. 10, FIG. 10 shows a radio frequency identification ("RFID") tag 1000, which may be employed to store and transmit a case code using an NFC technique. For example, after a user creates a new surgery and case code, an RFID tag 1000 may be programmed with the case code and supplied to the patient in a wearable device, such as a wristband 1100 shown in FIG. 11. In some examples, the RFID tag 1000 may be embedded within or affixed to a disposable plastic card, e.g., a credit-card sized card, and provided to one or more members of the surgical team assigned to the surgery. At the time of the surgery, the RFID tag may be scanned by a case code interface in communication with the robotic surgical system to provide the case code.

Figure 12:
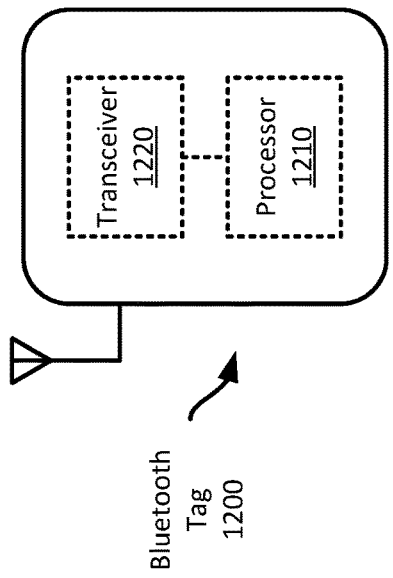
FIG. 12 shows an example Bluetooth tag to store and provide a case code for robotic surgery using multi-user authentication without credentials.

Referring to FIG. 12, in some examples, an electronic tag device 1200 that employs BT or BLE communication techniques may be programmed with the case code. For example, the example BT tag 1200 shown in FIG. 12 includes a processor 1210 with internal non-volatile memory (or that may be in communication with external non-volatile member) and a BT (or BLE) transceiver 1220. One or more BT tags 1200 may be programmed by the client computer 270 (or other computing device) shown in FIG. 2 and then distributed to members of the surgical team assigned to the surgery, or may be provided as a wearable device to a patient. Upon arriving at the assigned OR, the BT tag 1200 may pair with a BT transceiver embedded within a case code interface and provide the case code stored on the BT tag 1200.

Figure 13:
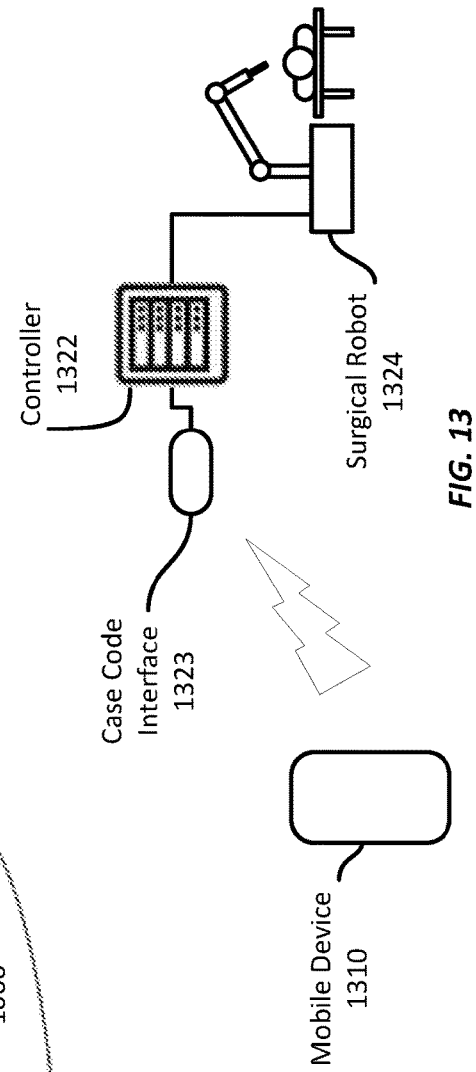
FIG. 13 shows an example mobile device to store and provide a case code for robotic surgery using multi-user authentication without credentials.

In some examples, rather than supplying a standalone RFID tag or BT (or BLE) tag device, a case code may be transmitted (or downloaded or otherwise provided) to one or more mobile devices carried by members of the surgical team. As discussed above, one or more such mobile devices may have an app installed to enable receipt of such case codes. Referring to FIG. 13, FIG. 13 shows an example mobile device 1310 configured to receive and store one or more case codes. For example, the mobile device 1310 may have one or more case codes pushed to it by a remote server after a new surgery has been created and the mobile device's user is assigned as personnel to the surgery.

After arriving in the OR for the surgery, the mobile device 1310 may use a wireless communication technique, such as BT, BLE, NFC, WiFi, etc. to establish communications with a case code interface 1323 of a robotic surgical system (illustrated as including a controller 1322, the case code interface 1323, and a surgical robot 1324). The mobile device 1310 may then provide the case code to the case code interface 1323, which communicates the case code to the controller 1322. The controller 1322 may validate the case code and then, using the case code, obtain other information associated with the surgery as will be described in more detail below.

Thus, various techniques may be employed according to different aspects to provide a case code to a surgical team or patient, and to communicate the case code to a robotic surgical system.

Figure 14:
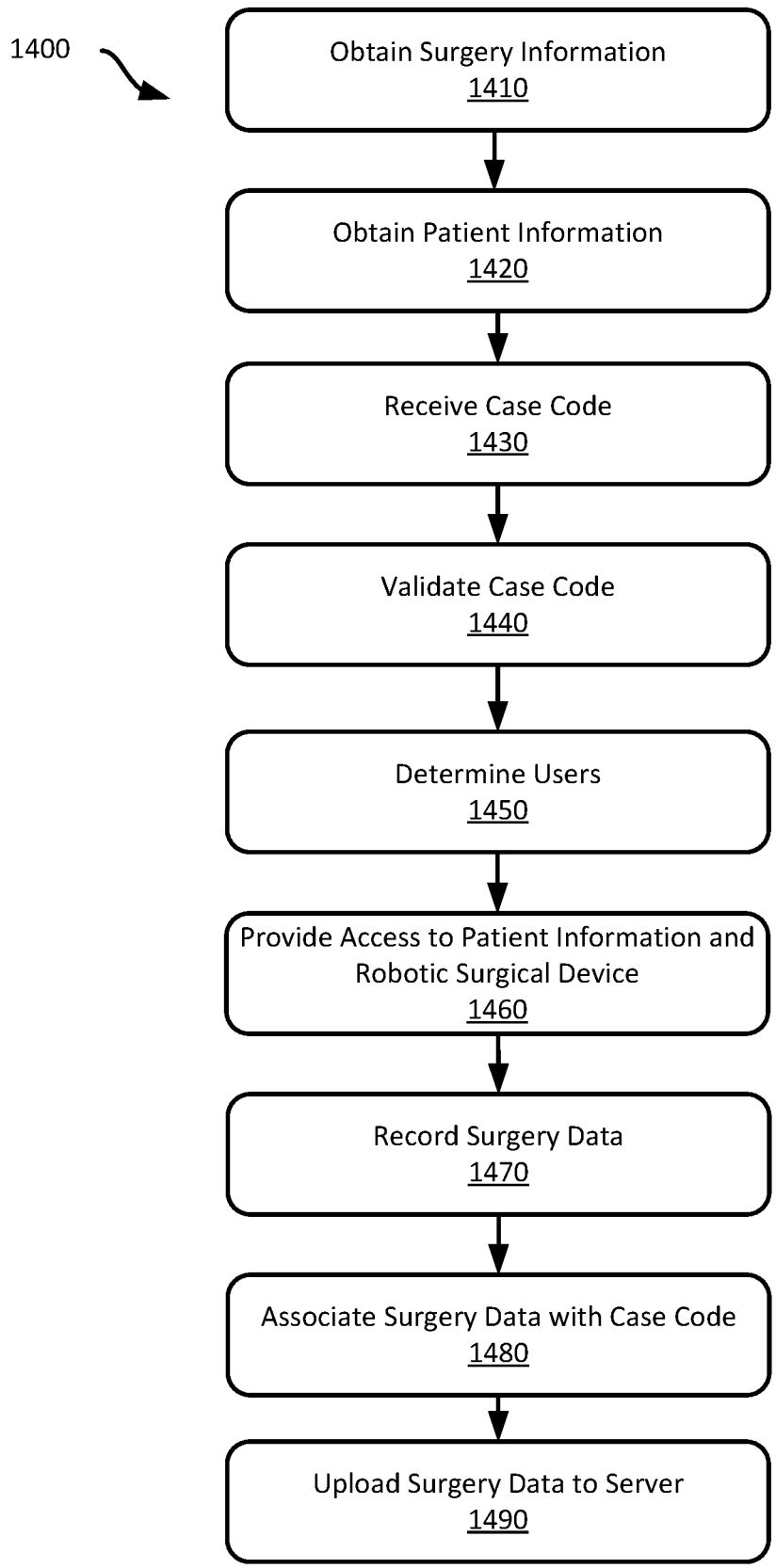
FIG. 14-15 show example methods for robotic surgery using multi-user authentication without credentials.

Referring now to FIG. 14, FIG. 14 shows an example method 1400 for robotic surgery using multi-user authentication without credentials. The example method 1400 will be discussed with respect to the example system 100 shown in FIG. 1, but may be employed according to any suitable system according to this disclosure, such as the example system shown in FIG. 2. In addition, the example method 1400 will be described with respect to a surgery created by a user of the client device 170 and stored in the data store 162 accessible by the remote server(s) 160.

At block 1410, the controller 130 obtains surgery information from the remote server(s) 160. In this example, after the controller 130 transmits the case code to the remote server(s) 160 and receives confirmation that the case code is valid and active, the controller 130 transmits a request to the remote server(s) 160 for information associated with the case code. In response to receiving the request for the information associated with the case code, the remote server(s) 160 accesses the data store 162, obtains information associated with the case code, and provides it to the controller 130.

In this example, the remote server(s) 160 obtains information about the surgical team, the patient, the procedure to be performed, the scheduled duration of the surgery, etc. from the data store 162. The remote server(s) 160 then transmits such information to the controller 130, which receives and stores, at least temporarily, the surgery information. In some examples, the remote server(s) 160 may only initially transmit patient records, if any, that do not include any confidential patient records, such as PHI. Such patient records may only include a patient ID number, which may be used to request other patient records, such as from one or more other remote data stores. In some examples, however, providing a valid and active case code may cause the remote server(s) 160 to provide confidential patient information to the robotic surgical system 110.

At block 1420, the controller 130 obtains one or more patient records. As discussed above, the controller 130 may request patient records from the remote server(s) 160, or patient records may be provided with the surgery information obtained at block 1410. In some examples, such as described above, the surgery information may include a patient ID number, but no other patient records or information. Thus, the controller 130 may request one or more patient records from the remote server(s) 160 or from other sources. Further, such an implementation may help ensure that patient information for one surgery is not inadvertently accessed during a different surgery.

In one example, surgery information may be provided from multiple different sources. For example, the remote server(s) 160 may have access to surgery information, such as the identities of the surgical team members, the type of surgery, and the date and time of the surgery, but may not have access to patient records. Thus, in some examples, the controller 130 may issue a further request to another remote server, such as a server located within the medical center or with an insurance provider, for one or more patient records, which may include confidential patient records. In such an example, if the controller 130 successfully validates the case code, it may then issue a request for one or more patient records, which may include the confidential patient information (e.g., PHI). However, if the controller 130 successfully validates the case code locally, but is unable to communicate with the remote server(s) 160 to ensure the case code is valid and active, it may not provide access to patient records having PHI. Thus, the robotic surgery system 110, when unable to communicate with the remote server(s) 160, may still allow the surgery to proceed after receiving an apparently valid case code, but deny full access to the surgery information, in particular, it may deny access to confidential patient information that may be protected by one or more confidentiality laws, e.g., HIPAA, unless and until it is able to receive confirmation from the remote server(s) 160 that the supplied case code is valid and active.

At block 1430, a case code is received. In this example, the case code is received by the case code interface 132 and provided to the controller 130 of the robotic surgical system 110. The case code interface, in this example, is a camera that is able to capture images of barcodes, including 1D and 2D barcodes. The camera is controlled by an application executing on the controller 130 that is able to detect the presence of such a barcode and to capture one or more images of the barcode in response to detecting its presence.

In other examples, the case code interface may include a barcode scanner, such as a laser-based barcode scanner. Alternatively, the case code interface 132 may include a wireless transceiver suitable for one or more wireless communication techniques. For example, the case code interface 132 may include an NFC reader device, a BT (or BLE) transceiver, or a WiFi access point. In such examples, the case code may be stored on an electronic device, such as an NFC tag, BT (or BLE) tag, or within memory of a mobile or other electronic device.

In the case of an NFC reader, an NFC tag or a mobile device with such capabilities, may be brought in range of the NFC reader. The NFC reader may then interrogate the NFC tag by generating and transmitting an electromagnetic field ("EMF") and receiving backscatter radiation that includes information, such as a case code; however any suitable NFC technique may be employed.

In an example using a BT or BLE technique, a BT (or BLE) tag or other electronic device, e.g., a mobile device, may be brought within range of the case code interface and detect a broadcast or advertisement signal from the case code interface 132. The tag may then receive the signal from the case code interface 132, and establish communications, e.g., by pairing with the case code interface 132. The case code 132 interface may then request the case code from the tag. Alternatively, in response to receiving the signal from the case code interface 132, the tag may transmit a response signal including a case code without establishing a pairing relationship. In a similar example employing WiFi, a mobile device may establish a WiFi connection with the case code interface 132 and then, in response to a request from the case code interface 132, provide the case code.

In some examples, the case code interface 132 may include a keyboard, a keypad, a touch screen, etc. that can receive user input. A user may then manually enter a case code. Further, while the example discussed above only includes one case code interface 132, any suitable number of case code interfaces 132 may be employed, such as to enable a broader array of ways to provide a case code to the robotic surgical system 110.

While a case code may be presented in its entirety in some examples, some examples may distribute portions of a case code to one or more members of the surgical team or to the patient. For example, a case code may be subdivided into four portions, three portinos supplied to members of the surgical team and a fourth provided as a barcode on a physical surgery file. Each team member may then present their respective portions of the case code to the case code interface 132, and the barcode on the physical file may be presented as well. Once all four portions of the case code have been presented, the full case code may be validated at block 1440.

At block 1440, the controller 130 validates the case code. In this example, validation of the case code involves multiple steps. The first step includes validating that the case code adheres to a recognized case code format. For example, a case code format may specify that a case code has M characters, the last N of which provide a checksum value for the first M-N characters of the case code. Thus, the controller 130 may check the length of the case code, and if the length is correct, it may verify that the checksum is correct. In some examples, the case code may be formatted to include, for example, a character representing a particular medical center and a second character representing a particular OR in the medical center. It may include some other specific information, such as a name of the head or surgery at the medical center, etc. In one such example, the robotic surgery system 110 may extract such information and validate that the robotic surgery system's configuration indicates that it is located at the medical center specified by the case code and is in the OR specified by the case code.

If the case code is not correctly formed, the controller 130 may output a notification that the case code is invalid. It may also deny access to the surgical robot and to any patient records available via the controller 130. Alternatively, if the controller 130 determines that the case code is properly formed, but specifies incorrect or incompatible information (e.g., it indicates a different OR than the robotic surgery system 110 is located in), the controller 130 may output a notification indicating the case code is valid, but may not be used with the robotic surgical system 110. In some examples, it may further indicate the reason for the error, e.g., that the case code specifies OR #3 while the robotic surgical system is located in OR #2. In one such example, the controller 130 may provide an option to override the error, e.g., a surgeon may indicate that the scheduled OR has changed, an emergency requires use of the present OR, etc.

A case code, in some examples, may persist indefinitely until used, though in some examples, it may expire even if it is never used. For example, a case code may expire the day after the scheduled surgery, or may have an expiration date encoded within it. Thus, the controller 130 may attempt to validate the case code, extract the expiration date, and determine whether the case code has expired based on the expiration date. If the case code is expired, the controller 130 may fail the case code validation.

After validating that the case code is correctly formed, the robotic surgical system 110 may transmit the case code to a remote server(s) 160 to validate that the case code exists in the system and is active. In response to transmitting the case code to the remote server(s) 160, the controller 130 may receive a response indicating that the case code is valid and active, at which time the controller 130 may output a notification indicating that the case code has been accepted. Alternatively, if the case code is not recognized by the remote server(s) 160 or that the case code is inactive, e.g., the case code has previously been used, that the case code is not scheduled to be used until the next day, etc. the controller 130 may output a notification indicating a problem with the case code, and may output additional information indicating the type of problem. In some examples, however, the robotic surgical system 110 may perform validation locally and not contact the remote server(s) 160 as described above.

In another example, the remote server(s) 160 may verify that the case code is valid and active, but that the case code specifies a different medical center or OR than is associated with the robotic surgery system 110. Thus, while the remote server(s) 160 may validate the case code, it may also transmit error information to the controller 130. The controller 130 may then display the error message, or provide the error information to a user's mobile device. In some examples the controller 130 may provide an option to override the error, or to otherwise proceed with the surgery despite the error. In some examples, however, the controller 130 may deny access to the robotic surgery system 110 based on the received error information. Further, the controller 130 may generate and transmit an alert if an incorrect case code is entered more than a predetermined number of times, e.g., 3 failed attempts. Such an alert may be sent to medical center administration, security, the head of surgery, etc.

In some examples, the controller itself may display information to a user using a display, or by illuminating an LED (e.g., a red or green LED) to indicate acceptance or rejection of a case code. Alternatively, for example, if the user has transmitted the case code to the controller from a mobile device, the controller 130 may transmit a message to the mobile device indicating acceptance or rejection of the case code, which may include additional information, such as information indicating a reason or reasons for rejection of the case code. The mobile device may then display such information to the user of the mobile device.

In some examples, the controller 130 may be unable to communicate with the remote server(s) 160. For example, a network link may be disabled, the remote server(s) 160 may be powered off or otherwise unavailable, etc. In such an example, the controller 130 may verify that the case code is properly formed, but may not be able to obtain further verification from the remote server(s). The controller 130 may still enable access to the robotic surgery system 110 based on a properly formed case code, but may operate in an anonymous mode or may have reduced functionality, for example, the robotic surgery system may not provide access to PHI. In some examples, the controller 130 may provide an indication of such a condition to the user or may transmit such information to the user's mobile device.

It should be appreciated that, while in this example the surgery information is received before the case code is entered, in some examples, the surgery information is not provided until an authorized, valid case code is received by the case code interface 132 and transmitted to the remote server(s) 160. In response to receiving the valid, authorized case code, the remote server(s) 160 may then transmit the surgery information to the robotic surgical system.

At block 1450, the controller 130 accesses the received surgery information to determine the personnel associated with the surgery. For example, the controller 130 may obtain identity information for one or more surgeons, one or more other doctors, one or more nurses or assistants, preference information or configuration settings for one or more surgical team members, etc. Such personnel information may be extracted from the surgery information and presented to the users of the robotic surgery system. The users may then use such information to identify a person operating the robotic surgical system 110. For example, at the beginning of the surgical procedure, a first surgeon may touch a touchscreen display on the controller to identify herself. The robotic surgery system 110 may then identify the time at which the first surgeon took control of the robotic surgery system 110. At a later time, a second person may take control of the robotic surgery system 110 and select their name as the operator. The robotic surgery system 110 may then change the active operator from the first surgeon to the second person. Such a feature may allow easy changes to personnel on-the-fly without requiring each different person to log into the robotic surgery system 110, e.g., with a username and password, each time the operator changes. Further, because the personnel information was obtained from the remote server(s) 160 as being associated with the surgery, each person is individually identified and authenticated to the robotic surgery system 110 through the use of the case code.

At block 1460, the controller 130 provides access to the robotic surgery device 134 and to the patient records. For example, the controller 134 may activate the robotic surgery device and enable one or more user interface devices to enable control over the robotic surgery device's functions. In addition, the controller 134 may provide access to the patient records obtained, such as those obtained at block 1450. Such patient records may be available for access from one or more terminals or display screens within the OR that are in communication with the controller 130. Thus, before (or while) a surgical team member operates the surgical robot 134, surgical team members may be able to review the patient records (or any other information relevant to the surgery) and provide guidance or planning for the surgery. However, as noted above, in some instances, access to the surgical robot may be provided even if patient information is not available.

At block 1470, the robotic surgery system 110 records data during the course of the surgery. The recorded data in this example includes the identity of the operators of the surgical robot 134, the times during which each operator was in control of the robot, information about movements and actions taken during the surgery, etc. In this example, the recorded data is stored locally at the controller 130; however, in some examples, the recorded data may be live-streamed to another location, such as to the remote server(s) 160, where the data may be viewed or stored. In some examples, the recorded data may both be stored locally at the controller and streamed to one or more other computing devices.

At block 1480, the recorded surgery data is associated with the case code. For example, if the controller 130 locally stores the recorded surgery data, it may store it in a way that is associated with the case code. For example, the recorded surgery data may be stored in filenames including part or all of the case code, in a folder having the case code as part or all of its name, in one or more database records with an association, e.g., a foreign key, identifying the case code, etc. In one example in which the recorded surgical data is streamed to another computing device, the streamed data may include the case code along with the recorded data.

At block 1490, the recorded surgery data is uploaded to the remote server(s) 160. In some examples as discussed above, the recorded data may be streamed in real-time, or near-real time, to the remote server(s) 160, and thus, block 1490 may not be a step separate from blocks 1470 and 1480. When the recorded surgery data is uploaded to the remote server(s) 160, the association with the case code is maintained, such as by identifying the case code when the upload is performed, or by providing information before or after the upload to indicate the associated case code.

After receiving the recorded surgery data, the remote server(s) 160 may store the recorded surgery data in the data store 162, or may provide the recorded surgery data to one or more other remote computing devices, such as one associated with the patient's health insurance or associated with one or more medical centers, such as to enable post-surgery communication with the patient.

It should be appreciated that the description of the method 1400 of FIG. 14 is merely one example sequence, and that one or more blocks of the method 1400 may be performed in different orders or may be omitted entirely. For example, as discussed above, if communication with the remote server(s) 160 is unavailable, the robotic surgery system 110 may allow access and use of the surgical robot 134, however, blocks 1430, 1440, 1450, and 1490 may be delayed or not performed at all. Further, validation of the case code in such a scenario may occur midway through a surgery if communications with the remote server(s) 160 is restored after surgery has begun. In such a case, errors related to validation of the case code by the remote server(s) 160 may be generated; however, such errors may not interrupt the surgery or otherwise disable access to the robotic surgical system 110.

Figure 15:
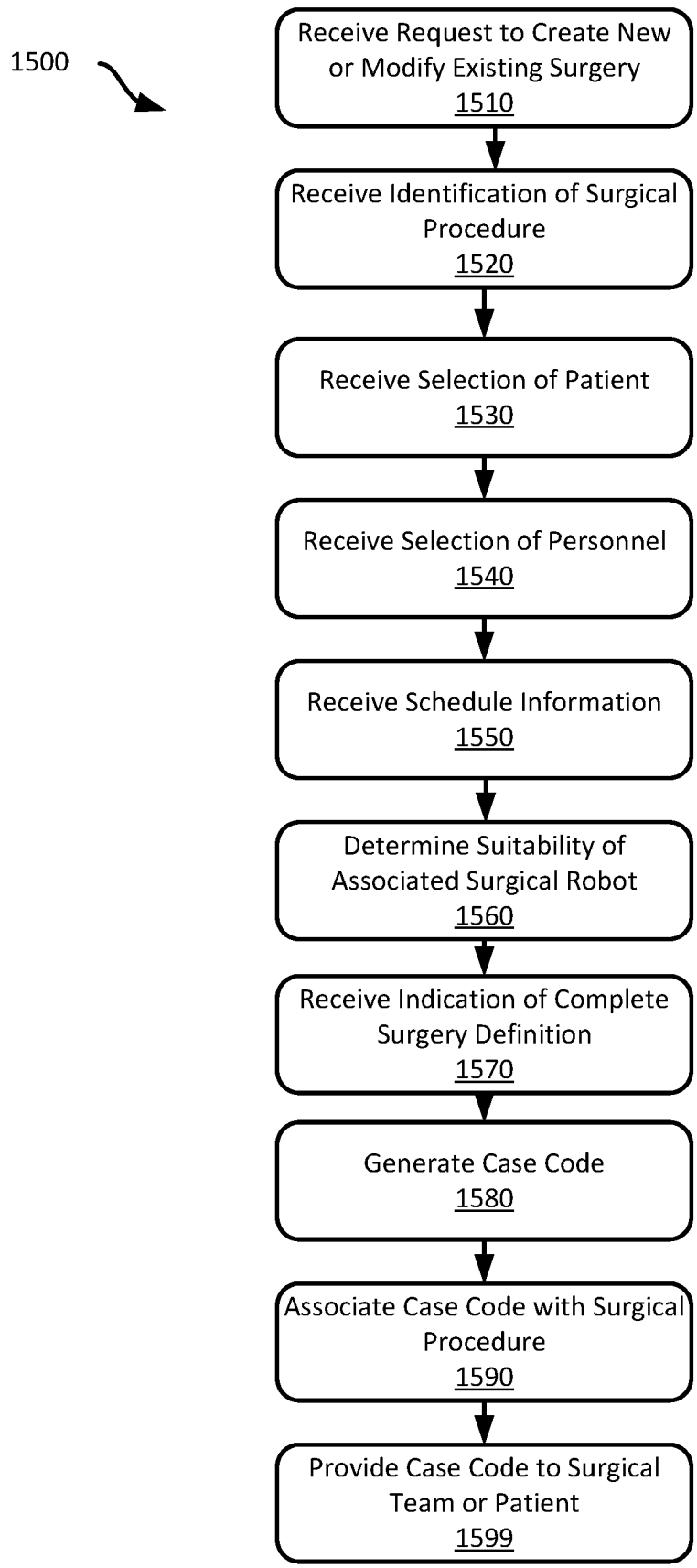

Referring now to FIG. 15, FIG. 15 shows an example method 1500 for robotic surgery using multi-user authentication without credentials. The example method 1500 will be discussed with respect to the example system 100 shown in FIG. 1, but may be employed according to any suitable system according to this disclosure, such as the example system shown in FIG. 2, and the example user interfaces 300-500 shown in FIGS. 3-5; however any suitable user interface may be employed according to different examples.

At block 1510, a user accesses a web portal or other software application and enters an input to create a new surgical procedure or modify an existing surgical procedure. The software application, e.g., a web portal, receives the user input, such as in response to the user selecting a menu item or an option displayed on a display screen to the user. In this example, the software application includes a web portal that the user accesses using a web browser. The software application is executed on a remote server(s) 160, but is presented to the user at the client device through the web browser. In some examples, however, the software application may be run locally on the user's client device, such as a desktop or laptop computer, mobile device, e.g., smartphone, pager, PDA, tablet, etc.

At block 1520, the software application receives an identification of a surgical procedure. For example, the user may select a procedure presented in a user interface, such as in the "Select Procedure" 310 portion of the user interface 300 shown in FIG. 3. If the user is modifying an existing procedure, she may make a similar selection, such as shown in the Select Procedure 510 portion of the user interface 500 shown in FIG. 5. In some examples, the user may manually type in the type of procedure to be created.

At block 1530, the software application receives a selection of a patient. In this example, the user may select a patient by typing, or selecting from a list, a patient identification number or by typing, or selecting from a list, a patient name. As is shown in FIGS. 3 and 5, the patient's name and ID number are displayed within the user interface 300, 500. In some examples, the user may scan a barcode associated with a patient to select the patient, such as may be printed or otherwise affixed to a physical patient file or record.

At block 1540, the software application receives a selection of personnel to participate in the surgery. For example, as may be seen in FIGS. 3 and 5, the software application may present a user interface 300, 500 that includes options 330-336, 530-536 to select one or more different persons to participate in the surgery. And while the examples shown only provide three different persons, it should be appreciated that the user interface may present any number of different person, such as via a list or menu, or may include functionality to enable searching for a user, such as via a search window. In addition, in some examples, the software application may filter the available personnel based on the type of surgery, the respective person's specialty (e.g., general surgery, anesthesiology, etc.), availability at a specified date and time, and/or the location of the surgery.

At block 1550, the software application receives scheduling information for the surgery. For example, the scheduling information may include a date and time for the surgery and a location for the surgery. The scheduling information may also include a duration of the surgery. Still other scheduling information may be obtained, such as equipment needed for the surgery, etc. In this example, a location for the surgery includes an identification of a medical center, such as in the Select Clinic/Hospital 320, 520 portion of the user interfaces 300, 500 in FIGS. 3 and 5, respectively, as well as an OR, such as may be selected using the Select Operating Room 340, 540 feature of the user interface 300, 500.

At block 1560, the software application determines the suitability of a surgical robot associated with the selected location for the surgery. In this example, after the user has selected the surgical procedure to be performed and has selected a medical center and OR, the software application accesses information to identify a surgical robot associated with the selected location and its respective capabilities. The software application, executed by the remote server(s) 160, accesses the data store 162 and obtains one or more records having information about the surgical robot associated with the selected location. The information about the surgical robot is then checked against the selected surgical procedure to determine whether the surgical robot can be used with the selected surgery. If the surgical robot is suitable, the software application in this example takes no further action; however, if the surgical robot is unsuitable, e.g., the surgical robot is an older version of a type of surgical robot or is simply the wrong kind of surgical robot for the selected type of surgery, it transmits a notification to the client device indicating that the selected location for the surgery has an incompatible surgical robot. In some examples, the software application may instead filter one or more options for medical centers or ORs to eliminate any having surgical robots that are incompatible with the selected surgery, or it may indicate preferred ORs, such as to schedule multiple short surgeries in succession in one OR, while leaving other ORs available for lengthier procedures. In some examples, the software application may not determine the suitability of the surgical robot, but may instead present the user with information about the surgical robot at the selected location to enable the user to assess the suitability of the surgical robot.

At block 1570, the software application receives an indication that the surgery definition is complete. In this example, the software application receives a user selection of an option to Save Surgery 350, 550 within the user interface 300, 500. However, any suitable option may be provided. In response to receiving such an indication, the software application creates a new surgery within the data store 162, associates the selected location with the surgery, associates the selected personnel with the surgery, and associates the selected patient with the surgery. In addition, the application identifies the selected location, personnel, and patient as unavailable for other surgeries during the scheduled date and time of the surgery.

At block 1580, the software application generates a case code for the surgery. As discussed above a case code may be generated according to one or more techniques to establish a string of alphanumeric characters. In this example, the software application that is self-authenticating in that it is possible to validate that the case code is properly formed without determining whether the case code is assigned to a valid surgery. As discussed above, techniques may generate case codes having one or more characters representing a checksum, whether as the last character(s), the first character(s), or at any location within the string of characters. Further, the checksum need not be set forth in successive or contiguous character positions, but instead may be scattered throughout the case code. In some examples, one or more other fields may include verifiable information, such as an indication of a medical center (e.g., a string of one or more characters) or an OR (e.g., a string of one or more characters) to be used for the robotic surgery. In some examples, the case code may include a portion of a patient identification number. For example, the case code may include a field corresponding to one or more characters of a patient's identity, such as an identification number, patient code, patient name, date of birth, social security number, etc.

In some examples, the case code may be a series of bytes or other data representing a value. For example, the case code may be a numeric value (e.g., a random number), a bit field, or a bit pattern. Further, example case codes may not be self-authenticating, but rather, may be data such as a patient's date of birth ("DOB"), a medical record number ("MRN"), or a combination of these two. For example, a case code may be a MRN concatenated with a patients DOB. Still other types of case codes may be employed in some examples. In some examples, a case code may be or include other information, such as a telephone number, e.g., a mobile phone number, for the head of the surgical team. Further, the case code may be generated using one or more cryptographic techniques. For example, the case code may be a value signed by a private key associated with a user. When the case code is then provided to the robotic surgical system, it can then authenticate the validity of the signature using the corresponding public key. In some cases, the cryptographic signature itself may be the case code, which can be authenticated using the corresponding public key and then also used to directly identify the corresponding surgical information. It should be appreciated that the broad term "case code" is not limited to self-authenticating codes or alphanumeric character strings. Rather, any suitable identifier may be employed according to different examples.

In one example, if a user is modifying a previously generated surgery, when the user makes her desired modifications, and saves the modified surgery, the system may generate a new case code to replate the previously generated case code. Such an example may be desirable to prevent use of the old case code, which may inadvertently obtain superseded surgery information. For example, if the original surgery information and case code were transmitted to the robotic surgery system, but later the surgery was modified by the user. If the new surgery information is not transmitted to the surgical robotic system, and the original case code were used, the surgical team would have no indication that the surgery information was out of date. However, in some examples, a new case code may not be generated following modifications to the surgery.

While some examples may provide only a single case code, in some examples, a case code may be generated and split into two or more portions that are each distributed to different members of the surgical team. Thus, when the surgical team arrives at the OR, each team member may supply their respective portion of the case code. Once all portions of the case code have been provided, the robotic surgical system may validate the case code.

At block 1590, the software application associates the case code with the surgery. For example, the case code may be stored as a record within the data store 162 and associated with the surgery. In some examples, the surgery may be assigned the case code as an identification number, such as in an identification number field of a database record.

At block 1599, the software application provides the case code to one or more members of the surgical team selected at block 1540 or the patient. For example, the software application may send the case code to the respective user(s) mobile device(s), which may then be accessed via an application installed on the mobile device(s). In some examples, the case code may be emailed to one or more members of the surgical team; it may be printed on a case file, patient record file, wristband, or other wearable device and provided to the patient; it may be stored on an NFC, BT, or BLE tag, printed on a surgery ticket, or otherwise physically manifested and provided to the surgical team or the patient. Still any other suitable technique may be used to provide the case code to the surgical team or patient. For example, the patient may be provided with a copy of the case code, which she may use to access information pre- or post-surgery, such as the scheduled surgery date, time, and location, or to review post-operative photos, results, video clips, etc.

It should be appreciated that while the blocks of the method 1500 are depicted and described in a particular order, no such ordering is required. For example, blocks 1520-1560 may be performed in any order or substantially simultaneously. Further, block 1580 may be performed at any time, including before any of blocks 1520-1570 are performed. For example, upon performing block 1510 to create a new surgery, a case code may be immediately generated at block 1580 and associated with the new surgery at block 1590 before any other actions are taken. Still further variations may be employed according to different examples.

Figure 16:
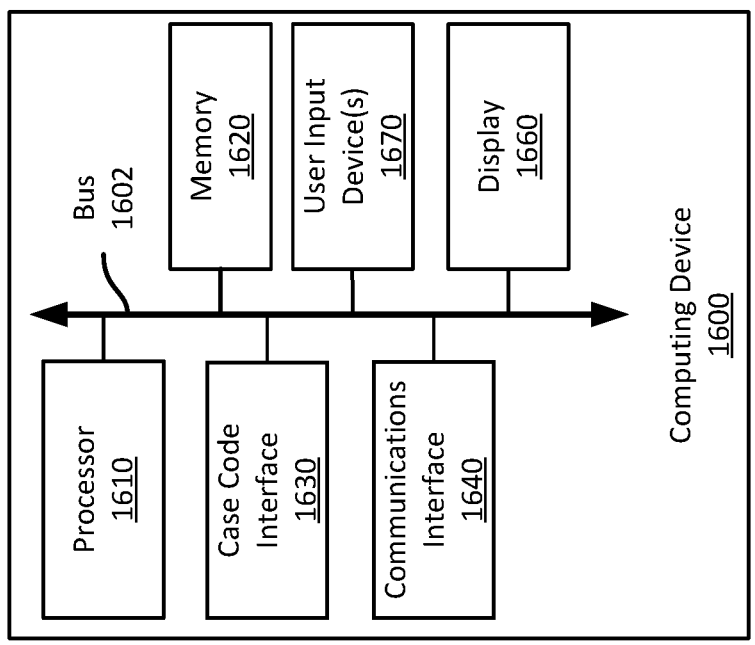
FIG. 16 shows an example computing device suitable for robotic surgery using multi-user authentication without credentials.

Referring now to FIG. 16, FIG. 16 shows an example computing device 1600 suitable for use in example systems or methods for robotic surgery using multi-user authentication without credentials according to this disclosure. The example computing device 1600 includes a processor 1610 which is in communication with the memory 1620 and other components of the computing device 1600 using one or more communications buses 1602. The processor 1610 is configured to execute processor-executable instructions stored in the memory 1620 to perform robotic surgery using multi-user authentication without credentials according to different examples, such as part or all of the example methods 1400, 1500 described above with respect to FIGS. 14 and 15. The computing device, in this example, also includes one or more user input devices 1670, such as a keyboard, mouse, touchscreen, microphone, etc., to accept user input. The computing device 1600 also includes a 1660 display to provide visual output to a user.

The computing device 1600 includes a case code interface 1630 to enable the computing device to receive one or more case codes, and may include any suitable case code interface discussed above. The computing device 1600 also includes a communications interface 1640. In some examples, the communications interface 1640 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
receiving, by a controller of a robotic surgical device from a case code interface device, a case code identifying a medical procedure, wherein the robotic surgical device comprises one or more articulating arms and is configured to assist in surgical procedures, wherein the robotic surgical device is communicatively coupled to the controller, the controller comprising one or more user interface devices to effect movement of the one or more articulating arms;
validating, by the controller, the case code based on a format of the case code, a configuration of the medical procedure specified by the case code, and a characteristic of the robotic surgical device, the case code identifying a surgical team and the medical procedure to be performed, wherein the case code comprises a backup code; and
responsive to validating the case code:
receiving an identification of a user of the robotic surgical device;
determining, by the controller, the user is authorized to perform the medical procedure associated with the case code based on the surgical team;
generating an alert based on the backup code;
denying access to one or more patient data records based on the backup code;
enabling, by the controller, the one or more user interface devices;
providing limited access, by the controller, to the user to control the robotic surgical device to enable a robotic surgical procedure; and
receiving, by the controller during the robotic surgical procedure, user inputs from the user interface devices and controlling the movement of the one or more articulating arms based on the user inputs.

2. The method of claim 1, wherein the case code is a self-authenticating case code or a cryptographically signed code.

3. The method of claim 1, further comprising:
obtaining, using the case code, one or more patient data records associated with the robotic surgical procedure, at least one of the patient data records comprising personalized health information ("PHI"), and
in response to validating the case code, providing access to the one or more patient data records to the one or more users.

4. The method of claim 1, further comprising, responsive to validating the case code:
obtaining, using the case code, identification information for each user of the one or more users; and
logging each user of the one or more users into the robotic surgical device.

5. The method of claim 4, receiving a user input indicating a first user of the one or more users is using the robotic surgical device, and changing an identity of an operating user to the first user.

6. The method of claim 5, further comprising recording surgical data during performance of the robotic surgical procedure and associating the first user with the surgical data.

7. The method of claim 6, further comprising:
receiving a second user input indicating a second user of the one or more users is using the robotic surgical device, and changing the identity of the operating user to the second user;
recording additional surgical data during performance of the robotic surgical procedure and associating the second user with the additional surgical data.

8. The method of claim 1, further comprising recording surgical data during performance of the robotic surgical procedure.

9. The method of claim 8, further comprising:
responsive to completing the robotic surgical procedure, completing recording the surgical data; and
transmitting the surgical data to a remote server.

10. The method of claim 9, wherein transmitting the surgical data to a remote server comprises associating identities of each user of the one or more users and one or more data records associated with the robotic surgical procedure with the surgical data, and transmitting the identities of each user of the one or more users and one or more data records to the remote server.

11. The method of claim 8, further comprising streaming, during the robotic surgical procedure, the surgical data to a remote server.

12. The method of claim 1, wherein determining the one or more users associated with the case code comprises receiving one or more user inputs identifying at least one user of the one or more users.

13. The method of claim 1, further comprising:
recording surgical data during performance of the robotic surgical procedure;
receiving a second case code, the second case code associated with a scheduled robotic surgical procedure;
determining a second set of one or more users associated with the second case code;
associating the surgical data with the scheduled robotic surgical procedure and the second set of one or more users; and
transmitting the surgical data and the associated second set of one or more users to a remote server.

14. The method of claim 1, wherein receiving the case code comprises at least one of (i) scanning a bar code, (ii) obtaining the case code from an RFID tag; (iii) obtaining the case code using a Bluetooth® communication technique, or (iv) receiving typed user input from a user input device.

15. The method of claim 1, wherein the robotic surgical procedure is a simulated medical procedure or a training exercise.

16. A system comprising:
a robotic surgical device comprising one or more articulating arms and configured to assist in surgical procedures;
a case code interface device;
a controller comprising one or more user interface devices to effect movement of the one or more articulating arms, the controller communicatively coupled to the robotic surgical device, the controller comprising a communications interface; a non-transitory computer-readable medium; and one or more processors configured to execute processor executable instructions stored in the non-transitory computer-readable medium to:

receive, from the case code interface device, a case code identifying a medical procedure;

validate the case code based on a format of the case code, a configuration of the medical procedure specified by the case code, and a characteristic of the robotic surgical device, the case code identifying a surgical team and the medical procedure to be performed, wherein the case code comprises a backup code; and responsive to validating the case code:
receive an identification of a user of the robotic surgical device;
determine the user is authorized to perform the medical procedure associated with the case code based on the surgical team;
generate an alert based on the backup code;
deny access to one or more patient data records based on the backup code;
provide limited access, by the controller, to the user to control the robotic surgical device to enable a robotic surgical procedure; and
receive, by the controller during the robotic surgical procedure, user inputs from the user interface devices and controlling the movement of the one or more articulating arms based on the user inputs.

17. The system of claim 16, further comprising a case code interface configured to (i) scan a bar code to obtain the case code, (ii) obtain the case code from an RFID tag; (iii) obtain the case code using a Bluetooth® communication technique, or (iv) receive typed user input from a user input device.

18. The system of claim 16, wherein the medical procedure is a simulated medical procedure or a training exercise.

19. The system of claim 16, wherein the processor is configured to execute further processor-executable instructions stored in the non-transitory computer- readable medium to:
obtain, using the case code, one or more patient data records associated with the robotic surgical procedure, at least one of the patient data records comprising personalized health information ("PHI"), and
in response to validating the case code, provide access to the one or more patient data records to the one or more users.

20. The system of claim 16, wherein the processor is configured to execute further processor-executable instructions stored in the non-transitory computer-readable medium to:

obtain, using the case code, identification information for each user of the one or more users; and
log each user of the one or more users into the robotic surgical device.

21. The system of claim 16, wherein the processor is configured to execute further processor-executable instructions stored in the non-transitory computer-readable medium to:
record surgical data during performance of the robotic surgical procedure;
responsive to completing the robotic surgical procedure, complete recording the surgical data; and
transmit the surgical data to a remote server.

22. A non-transitory computer-readable medium comprising processor-executable instructions configured to cause one or more processors to:
receive, by a controller of a robotic surgical device from a case code interface device, a case code identifying a medical procedure, wherein the robotic surgical device comprises one or more articulating arms and is configured to assist in surgical procedures, wherein the robotic surgical device is communicatively coupled to the controller, the controller comprising one or more user interface devices to effect movement of the one or more articulating arms;
validate, by the controller, the case code based on a format of the case code, a configuration of the medical procedure specified by the case code, and a characteristic of the robotic surgical device, the case code identifying a surgical team and the medical procedure to be performed, wherein the case code comprises a backup code; and
responsive to validating the case code:
receive an identification of a user of the robotic surgical device;
determine the user is authorized to perform the medical procedure associated with the case code based on the surgical team;
generate an alert based on the backup code;
deny access to one or more patient data records based on the backup code;
provide limited access, by the controller, to the user to control the robotic surgical device to enable a robotic surgical procedure; and
receive, by the controller during the robotic surgical procedure, user inputs from the user interface devices and controlling the movement of the one or more articulating arms based on the user inputs.

* * * * *